United States Patent [19]

Hamilton

[11] Patent Number: 5,036,841

[45] Date of Patent: Aug. 6, 1991

[54] SELF CONTAINED CLOSED CIRCUIT BREATHING APPARATUS

[75] Inventor: Robert M. Hamilton, Brea, Calif.

[73] Assignee: Computer Assisted Engineering, Orange, Calif.

[21] Appl. No.: 660,000

[22] Filed: Feb. 22, 1991

[51] Int. Cl.[5] .......................................... A61M 15/00

[52] U.S. Cl. ........................ 128/202.26; 128/205.12; 128/205.13; 128/205.17; 128/205.28

[58] Field of Search .................... 128/202.26, 205.12, 128/205.28, 205.13, 205.14, 205.17

[56] References Cited

U.S. PATENT DOCUMENTS

| | | | |
|---|---|---|---|
| 1,938,483 | 12/1933 | Christensen | 128/205.12 |
| 3,292,617 | 12/1966 | McDonough | 128/202.26 |
| 3,575,167 | 4/1971 | Michielsen | 128/205.28 |
| 4,163,448 | 8/1979 | Groward | 128/205.12 |
| 4,164,218 | 8/1979 | Martin | 128/202.26 |
| 4,273,120 | 6/1981 | Oswell | 128/205.12 |
| 4,362,153 | 12/1982 | Wilson et al. | 128/202.26 |
| 4,423,723 | 1/1984 | Winkler et al. | 128/205.12 |
| 4,498,470 | 2/1985 | Warncke | 128/202.26 |
| 4,879,996 | 11/1989 | Harwood, Jr. et al. | 128/205.12 |

*Primary Examiner*—Arron J. Lewis
*Attorney, Agent, or Firm*—Harold L. Jackson

[57] ABSTRACT

A closed circuit breathing apparatus for supplying breathable air to a facepiece to be worn by a user while working in an irrespirable atmosphere is disclosed. The apparatus includes an inhalation and an exhalation section connected to the facepiece. A $CO_2$ scrubber and a rebreather bag are connected in series between the inhalation and exhalation sections. A motorized fan is disposed in the inhalation section for continuously pumping air from the rebreather bag to the inhalation section. A pressure reducing valve supplies make up air from a tank of pressurized oxygen enriched air to the inhalation section. The fan and pressure reducing valve are arranged to supply sufficient air flow (e.g., 10 to 150 LPM) to the facepiece to maintain a positive face piece pressure under the anticipated normal use of the apparatus. A demand valve supplies additional air from the pressure reducing valve to the inhlation section to maintain a positive pressure at the facepiece during periods of peak demand (e.g. flow rates exceeding 150 LPM) and fan failure.

21 Claims, 2 Drawing Sheets

SELF CONTAINED CLOSED CIRCUIT BREATHING APPARATUS

BACKGROUND OF THE INVENTION

1. Field of the Invention

This invention relates to closed circuit breathing apparatus and more particularly to such an apparatus which provides a positive pressure at the facepiece of the wearer.

2. Description of the Prior Art

Self contained breathing systems designed to be worn on the back or front of a user such as a fireman which are generally classified as either closed circuit or open circuit types. Open circuit types are those in which exhaled or expired gases are discharged to atmosphere and not rebreathed. Open circuit systems are further divided into demand and pressure demand systems. In demand systems the pressure in the facepiece or facemask in relation to the immediate environment is positive during exhalation and negative during inhalation. In pressure demand systems the facepiece pressure in relation to the immediate environment is positive during both inhalation and exhalation.

Open circuit systems are simple and provide excellent protection and comfort. However, the high rate of gas usage and subsequent weight and size of the gas container required limit practical applications of such systems to a useful life of 30 to 45 minute duration. While open circuit systems are quite satisfactory for short term work, e.g., fighting limited fires, such systems do not provide the extended useful life (3–4 hours) required for long term work in a hostile environment, e.g., mine rescue operations.

Oxygen must be conserved in order to extend the life of a self contained breathing apparatus. A person converts only about 4% of the oxygen contained in the air into carbon dioxide. A closed circuit apparatus conserves oxygen by removing carbon dioxide from the exhaled gas and replenishing the spent oxygen so that the exhaled gas after regeneration can be rebreathed.

Prior art closed circuit systems such as the systems described in U.S. Pat. Nos. 4,362,153 ("'153 patent"), 4,879,996 ("'996 patent") and 4,498,470 ("'470 patent") while permitting extended use relative to open circuit systems either do not provide positive facepiece pressure at all times, i.e. during high inhalation rates or do so only through (1) the excessive use of pressurized air or oxygen thereby limiting the useful life or (2) the recirculation of untreated exhalation air thereby subjecting the wearer to possible carbon dioxide poisoning.

The '153 patent describes a system in which oxygen from a high pressure source is continuously supplied to a diffuser at a set rate of 5–30 liters per minute ("LPM") where it is mixed with regenerated air from a breathing bag and fed to the facepiece. The wearer presets one or more reducing valves connected to the pressurized oxygen tank to provide the desired flow rate. At rest a wearer will require about 7 to 10 LPM of air. During periods of strenuous activity the wearer will require from 100 to 150 or more LPM. If the reducing valve(s) of the '153 apparatus is set for at rest or light activity conditions, then the facepiece pressure will go negative during strenuous activity conditions. This will permit leakage of the ambient air into the facepiece. Such leakage is particularly hazardous in a closed system because it can lead to the build up of toxic gases. On the other hand, if the reducing valve(s) is set to deliver sufficient oxygen to provide positive facepiece pressure during periods of peak demand the useful life of the system will be greatly reduced.

The '966 patent describes a closed circuit system in which a spring loaded gas accumulator and counterlung are used to maintain a positive facepiece pressure. However, at peak demands, these items are augmented by a valve which bypasses a portion of the exhaled gas around the $CO_2$ scrubber so that such untreated exhaled air flows directly back to the facepiece. The patent points out that the $CO_2$ levels during periods high activity may reach 3% which level is above the maximum (i.e., 0.5%) dictated by federal and state regulations. Furthermore, if system leakage exceeds the preset flow rate of oxygen from the pressurized tank the system of the '966 patent will lose gas and become unable to supply the wearer's demand resulting in large negative pressures at the end of the inhalation cycle. In addition to the above disadvantages, the accumulation chambers would be relatively expensive and thus not disposable after use as a practical matter. The chambers would need to be sanitized after each use.

The '470 patent describes another closed circuit system in which a spring loaded breathing bag is employed to maintain a positive pressure at the facepiece. A source of pressurized air is supplied to the inhalation section to accommodate peak demand periods and/or leakage conditions. A separate source of pressurized oxygen and an oxygen sensor serve to maintain a preset oxygen ratio in the circulating air. The '047 system is even more complicated than the '966 patent and has many of the same deficiencies.

The above and other disadvantages of the prior art closed circuit systems are overcome by the present invention.

SUMMARY OF THE INVENTION

A self contained closed circuit breathing apparatus in accordance with the present invention includes a facepiece to be worn by personnel in a hostile or irrespirable atmosphere. The inlet end of a tubular exhalation section is connected to the facepiece. A carbon dioxide absorber or scrubber is connected between the outlet of the exhalation section and a rebreather reservoir for removing carbon dioxide from the exhaled air. A tubular inhalation section has its inlet end connected to the rebreather reservoir and its outlet end connected to the facepiece to provide a close loop passageway in which air may be circulated to and from the facepiece. An inhalation valve in the form of a check valve may be included in the facepiece or in the inhalation sections to assure no reverse flow of exhausted air into the inhalation section. A motor driven fan is disposed in the inhalation section for continuously pumping air from the rebreather reservoir through the inhalation section to the facepiece when the inhalation check valve if included is open or at least when the wearer is not exhaling in the absence of an inhalation valve.

A source of pressurized oxygen enriched gas (containing oxygen in excess of 20%) is connected through a pressure reducing valve to supply oxygen enriched air at a predetermined flow rate (e.g. 5–10 LPM) to the inhalation section to replenish the oxygen consumed by the wearer. The fan and the pressure reducing valve are arranged to provide a sufficient quantity of breathable air to the facepiece to provide a positive pressure in the facepiece under anticipated normal use conditions to thereby prevent the ingress of ambient air into the facepiece. A demand valve is also connected between the pressure reducing valve and the inhalation section to supply additional oxygen enriched gas to the inhalation section to maintain a positive pressure in the facepiece when the wearer's peak flow requirements exceed the flow rate provided by the fan and the first valve. A relief valve is disposed in the exhalation section for exhausting exhaled air to the atmosphere when the pressure in the exhalation section exceeds a predetermined value, e.g. one inch of water.

The features of the present invention can be best understood by reference to the following description, taken in conjunction with the accompanying drawings wherein like numerals indicate like parts.

DESCRIPTION OF THE PREFERRED EMBODIMENT

Figure 1:
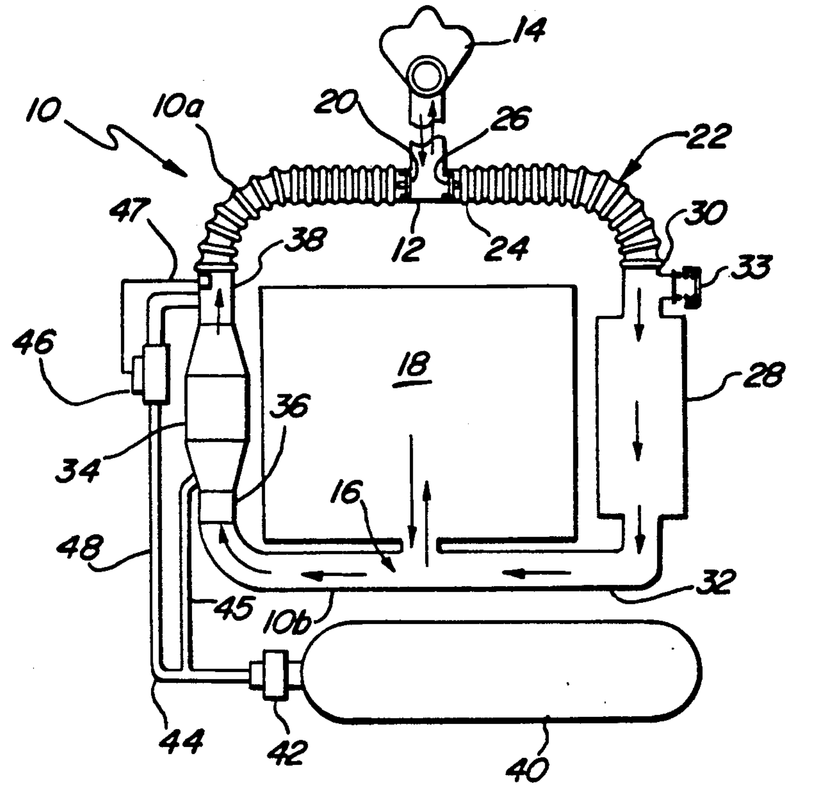
FIG. 1 is a schematic diagram of a closed circuit breathing apparatus constructed in accordance with the present invention.

Referring now to the drawings and particularly FIG. 1, the closed circuit breathing apparatus of this invention includes a tubular inhalation section indicated generally by reference numeral 10. The inhalation section 10 has an outlet end 12 adapted to be connected to a facepiece or face mask 14 and an inlet end 16 connected to a rebreather reservoir or bag 18. An inhalation check valve 20 may be included in inhalation section to assure that there is no reverse flow of exhaled air into the inhalation section. The inhalation section 10 has a flexible accordion portion 10 for accommodating movement of the facepiece 14.

A flexible tubular exhalation section 22 has its inlet end 24 connected to the facepiece 14 and may include an exhalation check valve 26. A $CO_2$ absorber or regenerator 28 is connected between the outlet end 30 of the exhalation section and the rebreather reservoir via duct 32 as illustrated for removing the $CO_2$ from the exhaled air. A relief valve 33, positioned at the outlet end of the exhalation section 22, is preferably set to open at a pressure of about 2" of water.

A motor driven fan 34 is disposed within the inhalation section for supplying a continuous stream of air to the facepiece when the inhalation valve is open as will be explained more fully. The fan 34 has an inlet 36 connected to the rebreather reservoir via a duct 10*b* which forms a portion of the inhalation section and an outlet 38 which is connected to the flexible duct 10 as shown.

A source of pressurized air in the form of a tank having an oxygen content in excess of 20% and preferably within the range of 25 to 35% by volume with the remainder consisting of nitrogen is shown at 40. A manually operated pressure reducing on/off valve 42 is secured to the air supply tank 40. The valve 42 supplies air at a reduced pressure to a manifold 44. A demand valve 46 senses the pressure in the inhalation section 10 via line 47 and bleeds additional pressurized air from the manifold 44 and line 45 into the section adjacent the fan outlet if needed to maintain the pressure at the facepiece above ambient, preferably above 1" of water. If desired, the demand valve 46 may have a pressure reducing capability and be connected directly to the tank 40.

Figure 2:
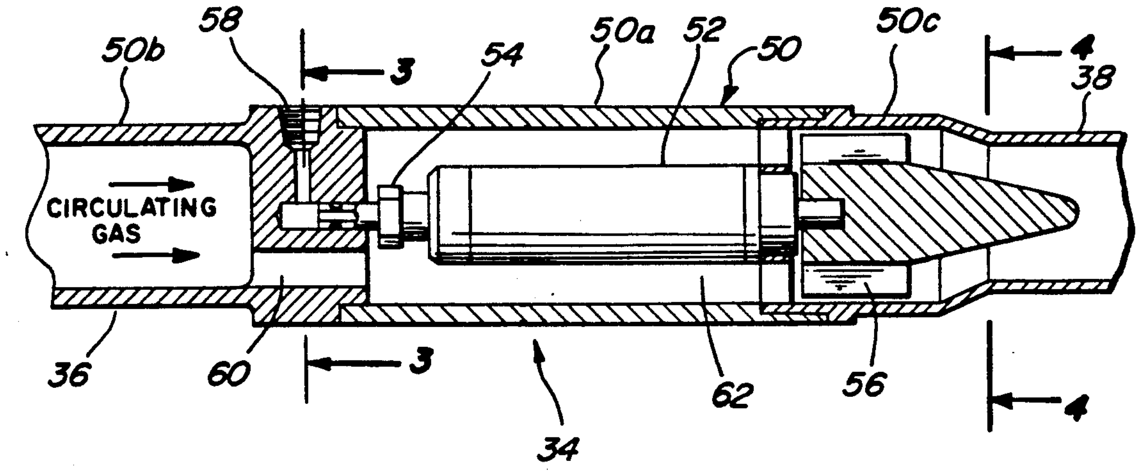
FIG. 2 is a cross-sectional view of a motorized fan for use in the apparatus of FIG. 1.
Figure 3:
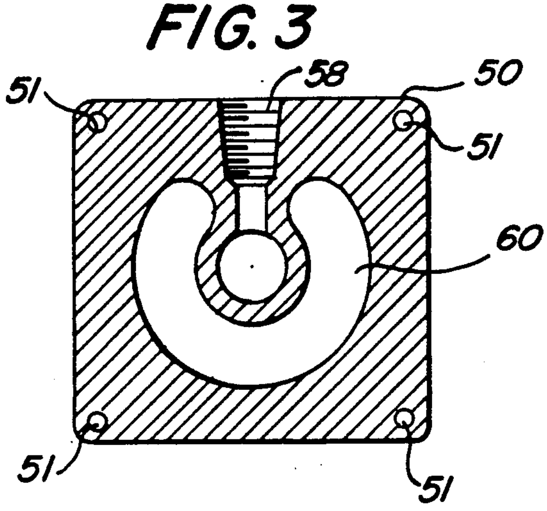
FIG. 3 is a cross-sectional view of the motor/fan of FIG. 2 taken along lines 3—3.
Figure 4:
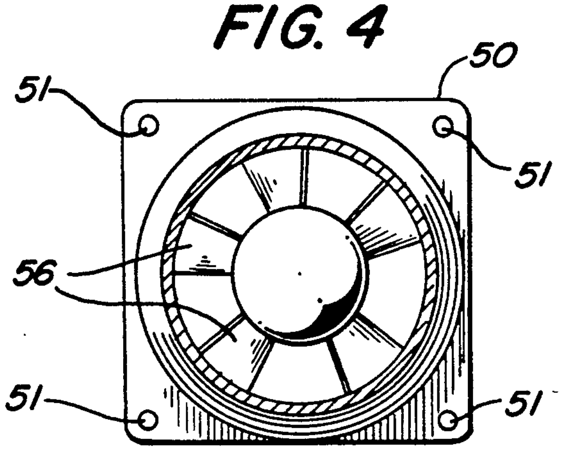
FIG. 4 is a cross-sectional view of the motor/fan of FIG. 2 taken along lines 4—4.

Referring now to FIGS. 2-4, the motorized fan 34 employed in the apparatus of FIG. 1 includes a housing 50 in which a rotor 52 is rotatably mounted. The housing comprises a center section 50*a* secured between end piece 50*b* and 50*c* by bolts (not shown) extending through bores 51 (FIGS. 3 and 4). A turbine 54 is mounted on the upstream side of the rotor and a fan 56 is mounted on the downstream side as shown. Air from the rebreather reservoir 18 is drawn into the fan through inlet 60 in the end piece 50*b* and intermediate chamber 62 in the center section 50*a*. High pressure air from the reducing valve 42 is supplied to inlet port 58 via manifold 44 and line 48 and directed by suitable nozzles (not shown) against the turbine 54 to drive the rotor 52 and fan 56. The high pressure air from the tank 40 thus supplies the energy to drive the fan 56. The pressurized air after passing though the turbine mixes with air from the rebreather reservoir 18 in chamber 62 and thus provides the necessary make up oxygen and air. I have found that a preferred flow rate of pressurized air from the valve 42 through the line 45 is about 5 to 10 LPM. While a turbine motor 54 is illustrated for driving the fan 56, a vane type or other gas driven motor could also be used for the purpose.

The fan continuously circulates air from the rebreather reservoir through the inhalation section 10, the facepiece 14, the exhalation section 22 and the $CO_2$ scrubber 28 at least in the absence of exhalation. Typically the motor/fan 34 will provide a continuous flow of air at the rate of 7 to 10 LPM through the closed loop system when the wearer is not inhaling or exhaling. The pressure drop across the motor/fan 34 remains about constant so that when the wearer inhales, thereby reducing the back pressure on the motor/fan, the flow rate will increase (e.g. 15 to 150 LPM) and when the wearer exhales the flow rate through the motor/fan will decrease or stop. It should be noted that the inhalation and exhalation valves are optional since the continuous air flow through the motor/fan will minimize of eliminate the reverse flow of air.

The motor/fan 34 and the pressure reducing valve 42 when adjusted as discussed above will provide a sufficient quantity of breathable air to the facepiece 14 to provide a positive pressure in the facepiece under anticipated normal use conditions (i.e., 7-150 LPM) to thereby prevent the ingress of ambient air into the facepiece.

If the peak demand exceeds the flow rate through the motor/fan 34 or in the event of a fan failure, the demand valve will open to maintain a positive pressure at the facepiece. Preferably the demand valve 42 is adjusted to open at a sensed pressure 1" of water as discussed previously. However, the valve 46 may be set to open at any pressure above ambient, e.g. 0" to 2" of water The demand valve thus serves a dual function of providing a supplemental flow in the event that peak flow requirements exceed the circulating flow and of providing a redundant flow path of breathable air in the event of a motor/fan failure.

The relief valve 33, being positioned between the facepiece and the $CO_2$ absorber, insures that gas being discharged will be that air which has the highest $CO_2$ content i.e. the air exhaled from the deeper recesses of the lungs. The discharged air through the relief valve may represent as much as 15-20% of the $CO_2$ generated in the lungs. The removal of this $CO_2$ helps lower the system temperature since the removal of $CO_2$ by the absorber 28 involves an exothermic reaction.

The use of a motor/fan for circulating the air through the system to maintain a positive pressure at the facepiece during normal anticipated activity by the wearer greatly increases the useful life of the system while the use of the oxygen make-up gas to drive the motor/fan conserves energy. The rebreather reservoir 18 can be in the form of a disposable bag to eliminate the need for sanitization after each use. The use of an oxygen enriched air mixture consisting of 25 to 35% oxygen insures that the circulating air will never have an oxygen content of greater than that percentage. I have found that an oxygen content of about 30% is ideal for most applications.

Figure 5:
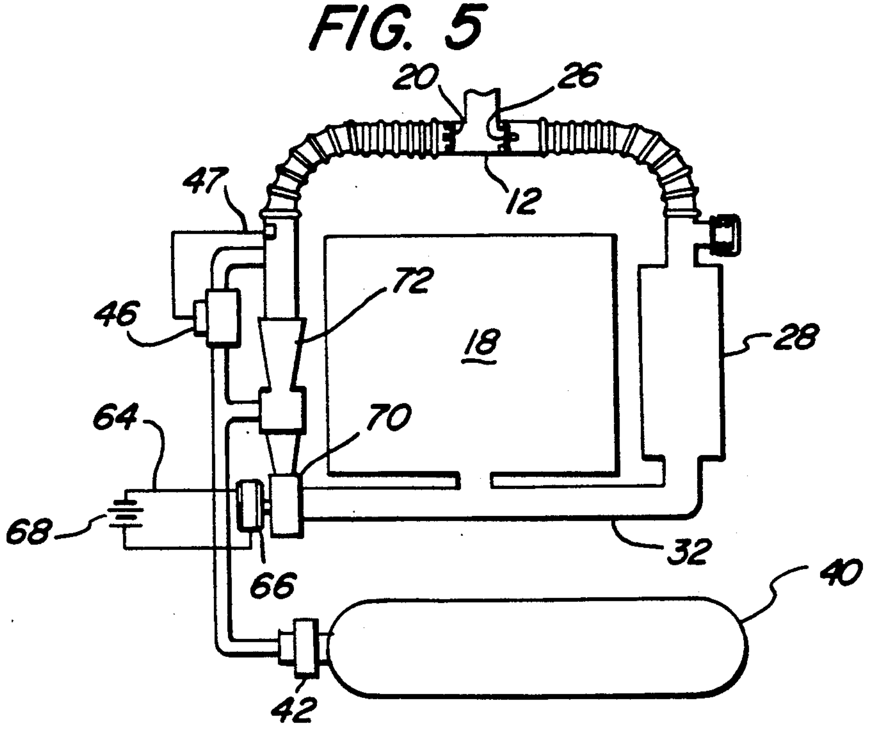
FIG. 5 is a schematic diagram of another embodiment of a closed circuit breathing employing a battery operated motor/fan.

Another embodiment of the invention is illustrated in FIG. 5 in which a battery operated motor/fan 64 is used in lieu of the turbine operated fan 34 of FIG. 1. The motor fan 64 comprises an electric motor 66 which operates from a battery 68 and drives a squirrel cage fan 70 positioned in the inhalation section 10 as shown.

The output of the fan 70 is directed to the facepiece through a diffuser 72. The supplemental gas from the tank 40 is also supplied to the diffuser as illustrated. The flow rates of the gas through the fan 70 and from the tank 40 may be the same as discussed with respect to the apparatus of FIG. 1.

There has been described a personal closed circuit breathing apparatus which provides a positive facepiece pressure for maximum protection of the wearer and extended useful life and added safety to redundant flow paths.

Various modifications will be apparent to those skilled in the art without involving any departure from the spirit and scope of my invention as defined in the appended claims.

What is claimed is:

1. A self contained closed circuit breathing, apparatus comprising:

a) a facepiece;

b) an inhalation section having an outlet end connected to the facepiece and a inlet end;

c) an exhalation section having an inlet end connected to the facemask and an outlet end;

d) a rebreather reservoir;

e) carbon dioxide absorber means connected between outlet end of the exhalation section and the rebreather reservoir for absorbing carbon dioxide from the exhaled air prior to its passage into the rebreather reservoir;

f) a motor driven fan disposed in the inhalation section, the fan being arranged to continuously pump air from the rebreather reservoir through the inhalation section and the facepiece at least when the wearer is not exhaling;

g) a source of pressurized breathable gas containing oxygen in excess of 20% by volume;

h) pressure reducing valve means connected to the pressurized gas source and the inhalation section, the fan and pressure reducing valve means being arranged to provide a pressure in the facepiece which is equal to or exceeds the ambient air pressure under anticipated normal use conditions of the apparatus for preventing the ingress of ambient air into the facepiece;

i) demand valve means connected between the pressure reducing valve means and the inhalation section and operable to supply additional gas to the inhalation section to maintain the pressure at the facepiece at or above ambient pressure when peak flow requirements exceed the flow rate provided by the fan and pressure reducing valve means; and j) a relief valve disposed in the exhalation section for exhausting exhaled air to atmosphere when the pressure in the exhalation section exceeds a predetermined value.

2. The invention of claim 1 wherein the demand valve means is arranged to maintain the pressure within the facepiece within the range of 0 to 2 inches of water.

3. The invention of claim 2 wherein the demand valve is arranged to open when the pressure within the inhalation section is about 2 inches of water.

4. The invention of claim 2 wherein the fan motor is operated by gas from the pressure reducing valve means.

5. The invention of claim 4 wherein the fan motor comprises a gas turbine.

6. The invention of claim 5 wherein the gas from the turbine is mixed with the air from the rebreather reservoir.

7. The invention of claim 2 wherein the fan is arranged to provide a flow rate of air within the range of about 10 to 150 LPM dependent upon the air demands of the wearer.

8. The invention of claim 4 wherein the relief valve is arranged to open and exhaust exhaled gas to atmosphere when the pressure within the exhalation section exceeds about 2 inches of water.

9. The invention of claim 2 wherein the fan motor is battery operated.

10. The invention of claim 4 wherein the pressure reducing valve means is arranged to supply gas to the turbine within the range of about 5 to 10 liters LPM.

11. The invention of claim 10 wherein the pressure reducing valve means supplies about 7.5 liters of gas per minute to the turbine.

12. The invention of claim 3 further including an inhaling valve for preventing exhaled air from flowing into the inhalation section.

13. A self contained closed circuit breathing apparatus for supplying breathable air to a facepiece to be worn by a user while in an irrespirable atmosphere, comprising:

a) an inhalation section having an inlet and outlet end, the outlet end being connected to me facepiece;

b) an exhalation section having an inlet and outlet end, the inlet end being connected to me facepiece;

c) an inhalation valve disposed in the inhalation section for preventing the flow of exhaled air into the inhalation section;

d) a rebreather bag;

e) a regenerator connected between the outlet end of the exhalation section and the rebreather bag for removing carbon dioxide form the exhaled air;

f) a fan disposed in the inhalation section for continuously circulating air from the rebreather bag through the inhalation section and the facepiece, the exhalation section and the regenerator when the inhalation valve is open;

g) a source of pressurized oxygen enriched air;

h) first valve means connected between the pressurized air source and the inhalation section, the fan and the first valve means being arranged to provide a positive pressure at the facepiece under anticipated normal use conditions;
i) pressure sensing means disposed in the inhalation section downstream from the fan;
j) second valve means coupled between the pressurized air source and the inhalation section and responsive to the pressure sensing means for supplying additional air to the inhalation section to maintain a positive pressure at the facepiece when the user's air demand exceeds the flow rate provided by the fan and first valve means; and
k) a relief vale disposed in the exhalation section for exhausting exhaled air to atmosphere when the pressure in the exhalation sections exceeds a predetermined value.

14. The breathing apparatus of claim 13 wherein the fan includes a turbine and wherein the first valve means supplies pressurized air to the turbine.

15. The breathing apparatus of claim 14 wherein the fan is arranged to supply air to the inhalation section when the inhalation valve is open at the rate of about 10 to 150 LPM.

16. The breathing apparatus of claim 15 wherein the first valve means is arranged to supply air to the turbine at a flow rate of about 5 to 10 LPM.

17. The breathing apparatus of claim 14 wherein the first valve means is arranged to supply about 7.5 LPM's of air to the turbine.

18. The breathing apparatus of claim 16 wherein the relief valve is arranged to open when the pressure within the exhalation section is within the range of about 1 to 2 inches of water.

19. The breathing apparatus of claim 16 wherein the second valve means is arranged to open when the pressure sensing means senses a pressure of about 1 inch of water.

20. The breathing apparatus of claim 14 wherein the fan includes an electric motor.

21. The breathing apparatus of claim 12 further including an exhalation valve for preventing exhaled air in the exhalation section from entering the facepiece during inhalation.

* * * * *